US008080049B2

(12) United States Patent
Zukowski et al.

(10) Patent No.: US 8,080,049 B2
(45) Date of Patent: Dec. 20, 2011

(54) BRANCHED STENT DELIVERY SYSTEM

(75) Inventors: Stanislaw Zukowski, Flagstaff, AZ (US); Eric Gerard Johnson, Flagstaff, AZ (US)

(73) Assignee: Gore Enterprise Holdings, Inc., Newark, DE (US)

( * ) Notice: Subject to any disclaimer, the term of this patent is extended or adjusted under 35 U.S.C. 154(b) by 964 days.

(21) Appl. No.: 11/595,150

(22) Filed: Nov. 9, 2006

(65) Prior Publication Data
US 2007/0299495 A1    Dec. 27, 2007

Related U.S. Application Data

(63) Continuation of application No. 11/474,165, filed on Jun. 23, 2006, now Pat. No. 7,771,465.

(51) Int. Cl.
*A61F 2/06* (2006.01)
(52) U.S. Cl. ....................................... 623/1.11
(58) Field of Classification Search ............ 600/585
See application file for complete search history.

(56) References Cited

U.S. PATENT DOCUMENTS

| | | | | |
|---|---|---|---|---|
| 5,676,697 | A * | 10/1997 | McDonald | 623/1.35 |
| 5,824,055 | A * | 10/1998 | Spiridigliozzi et al. | 623/1.11 |
| 6,099,558 | A * | 8/2000 | White et al. | 623/1.16 |
| 6,283,991 | B1 * | 9/2001 | Cox et al. | 623/1.13 |
| 6,537,284 | B1 | 3/2003 | Inoue | 606/108 |
| 6,579,309 | B1 * | 6/2003 | Loos et al. | 623/1.16 |
| 6,645,242 | B1 | 11/2003 | Quinn | 623/1.16 |
| 6,663,665 | B2 * | 12/2003 | Shaolian et al. | 623/1.35 |
| 6,669,718 | B2 | 12/2003 | Besselink | 623/1.11 |
| 6,689,157 | B2 * | 2/2004 | Madrid et al. | 623/1.11 |
| 7,959,667 | B2 * | 6/2011 | Ta et al. | 623/1.35 |
| 2002/0049412 | A1 * | 4/2002 | Madrid et al. | 604/164.05 |
| 2002/0077692 | A1 | 6/2002 | Besselink | |
| 2002/0120327 | A1 * | 8/2002 | Cox et al. | 623/1.16 |
| 2002/0156516 | A1 * | 10/2002 | Vardi et al. | 623/1.11 |
| 2003/0065375 | A1 * | 4/2003 | Eskuri | 623/1.11 |
| 2003/0093109 | A1 * | 5/2003 | Mauch | 606/194 |
| 2004/0002714 | A1 * | 1/2004 | Weiss | 606/108 |
| 2004/0098084 | A1 | 5/2004 | Hartley et al. | 623/1.11 |
| 2004/0127975 | A1 * | 7/2004 | Levine et al. | 623/1.35 |
| 2004/0158307 | A1 * | 8/2004 | Jones et al. | 623/1.11 |
| 2005/0033400 | A1 * | 2/2005 | Chuter | 623/1.11 |
| 2005/0033402 | A1 * | 2/2005 | Cully et al. | 623/1.11 |
| 2005/0245941 | A1 * | 11/2005 | Vardi et al. | 606/108 |
| 2005/0267442 | A1 * | 12/2005 | Von Oepen | 604/509 |
| 2007/0078506 | A1 * | 4/2007 | McCormick et al. | 623/1.11 |
| 2008/0172122 | A1 * | 7/2008 | Mayberry et al. | 623/1.15 |

FOREIGN PATENT DOCUMENTS

| | | |
|---|---|---|
| WO | WO 01/74270 | 10/2001 |
| WO | WO 02/30329 | 4/2002 |
| WO | WO 2004/019823 | 3/2004 |

\* cited by examiner

*Primary Examiner* — Gary Jackson
*Assistant Examiner* — Amy Shipley
(74) *Attorney, Agent, or Firm* — Gilbert R. Gabo

(57) ABSTRACT

An interventional delivery system with a first catheter having at its distal end a side branch vessel segment; a second catheter attached around the first catheter and having at its distal end a main vessel segment; a side branch vessel device attached to side branch vessel segment of the first catheter; and main vessel device attached to the main vessel segment of the second catheter. The main vessel device and the side branch vessel device are able to be simultaneously delivered to a treatment site.

8 Claims, 18 Drawing Sheets

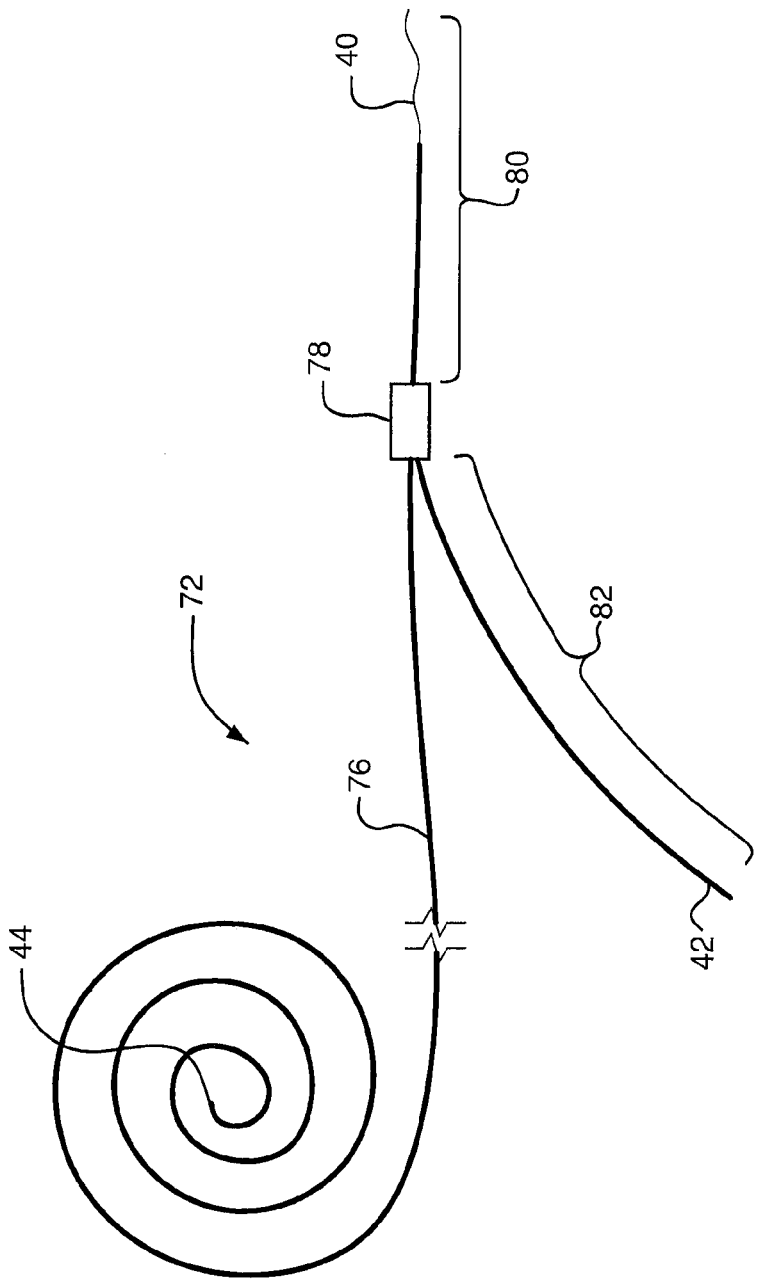

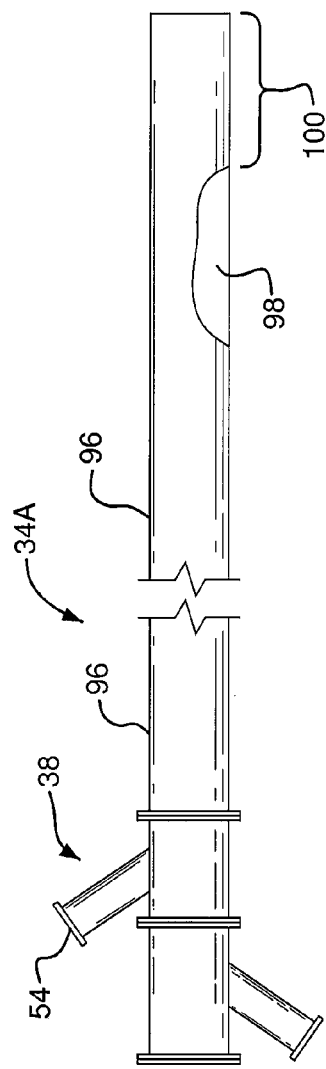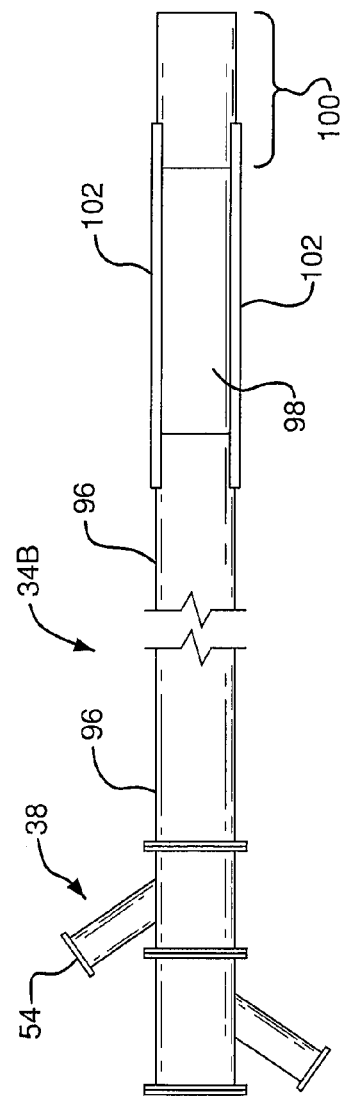

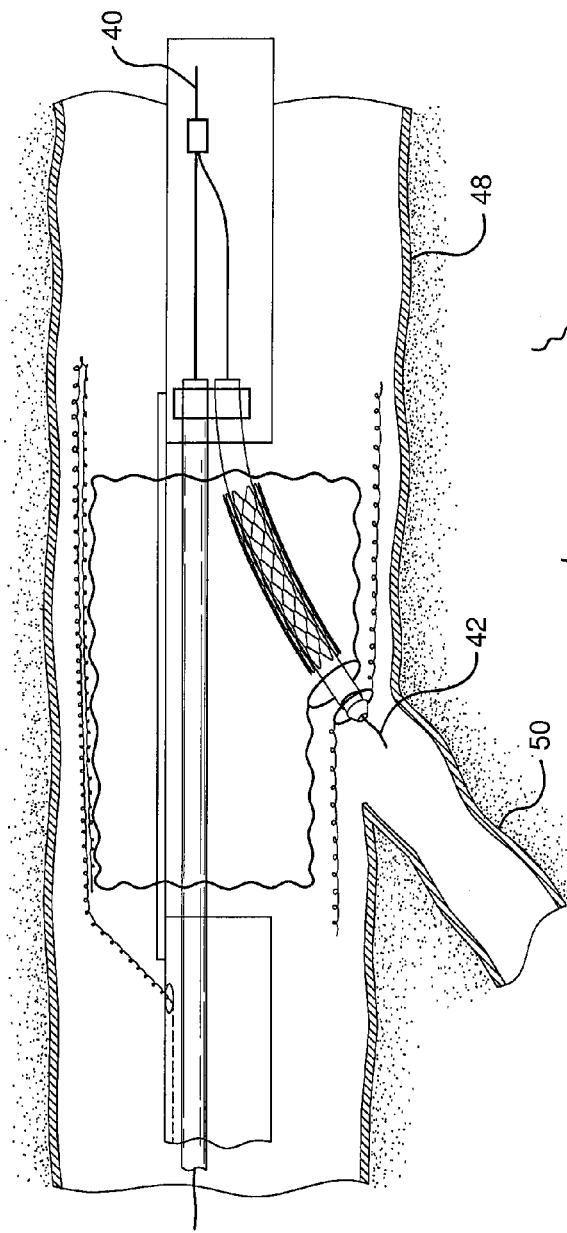
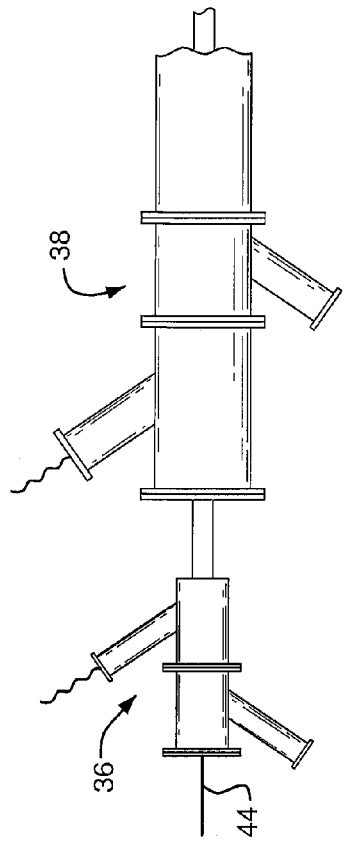
FIG.10A
FIG.10B

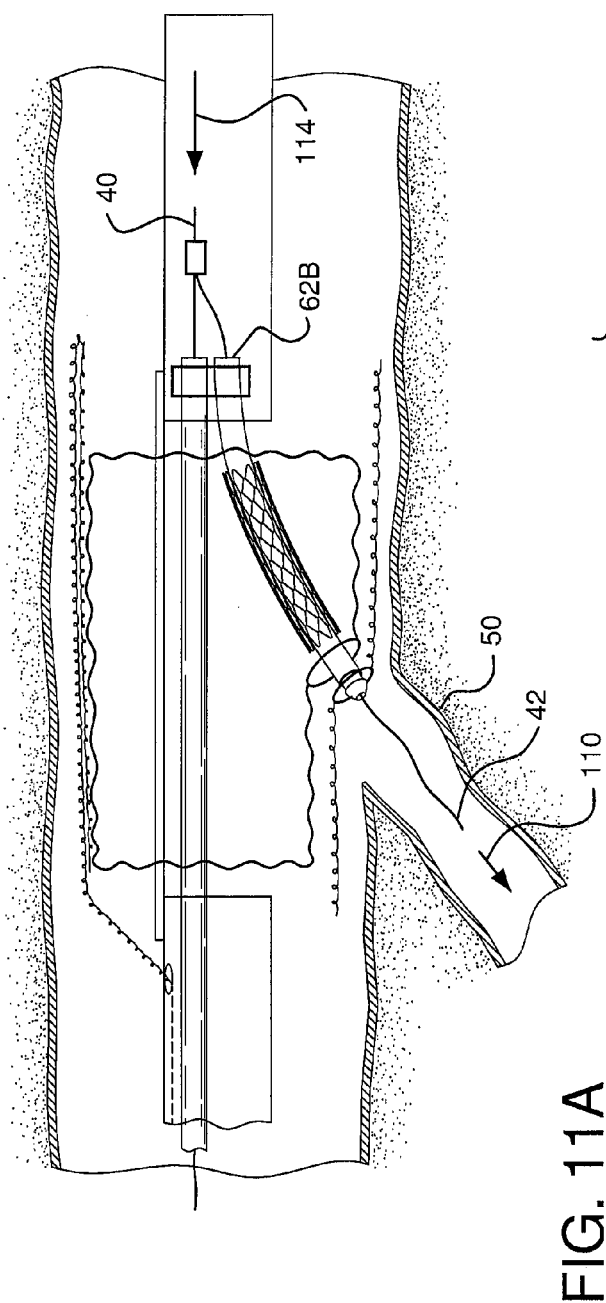
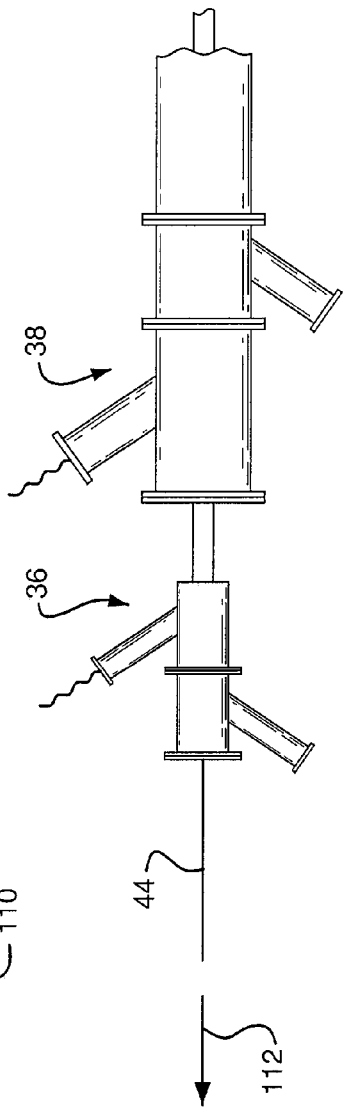
FIG. 11A
FIG. 11B

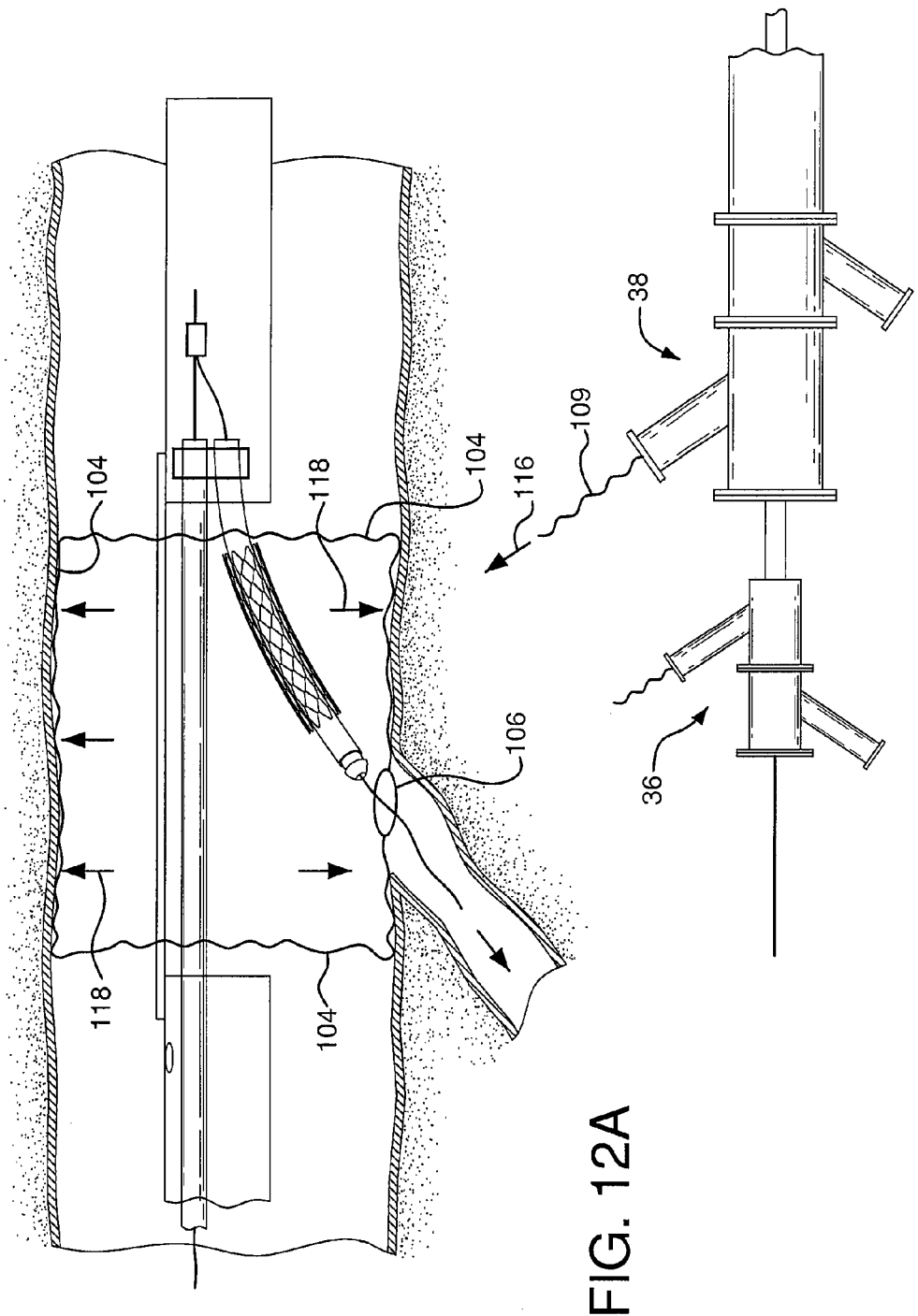

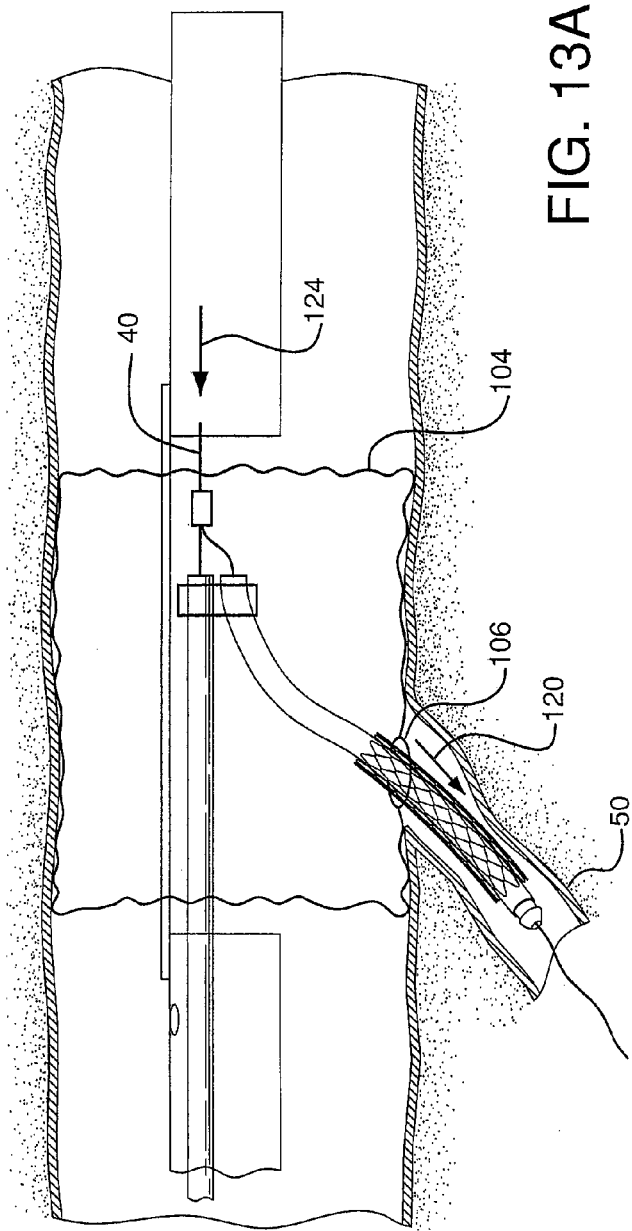
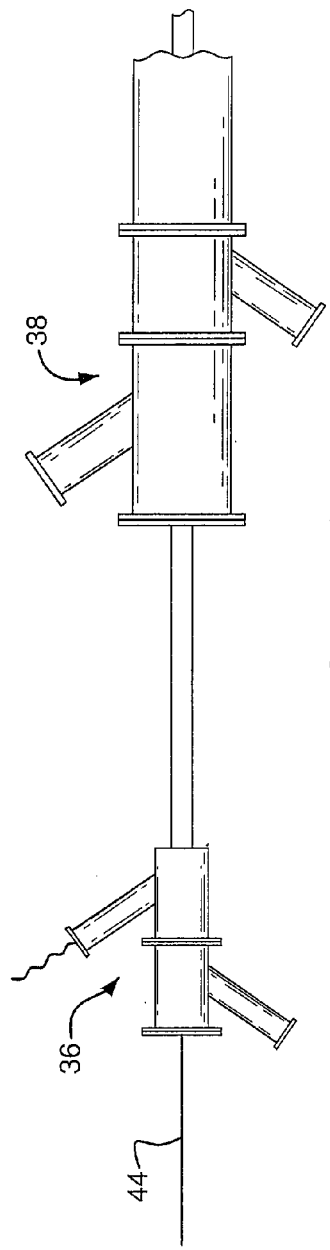
FIG. 13A
FIG. 13B

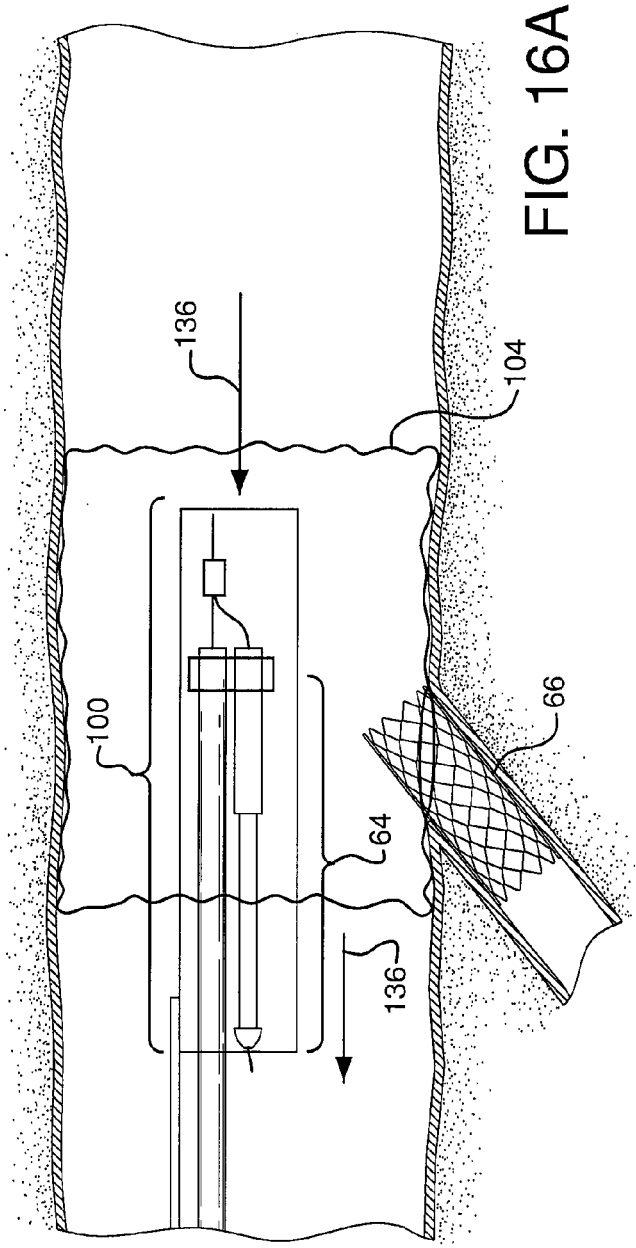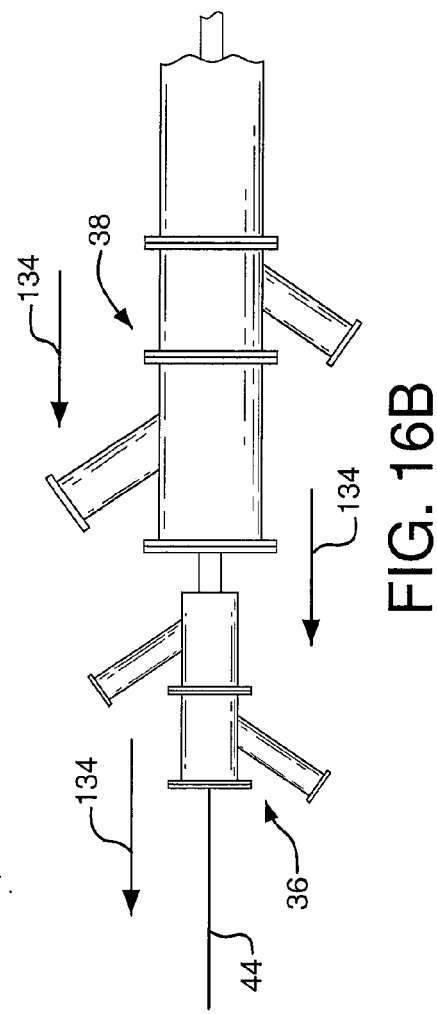

BRANCHED STENT DELIVERY SYSTEM

CROSS REFERENCE TO RELATED APPLICATIONS

This application is a continuation of commonly owned and U.S. patent application Ser. No. 11/474,165 filed Jun. 23, 2006 now U.S. Pat. No. 7,771,465.

BACKGROUND OF THE INVENTION

The present invention generally relates to a delivery system and method for delivering an expandable endoluminal prosthetic device such as a stent graft and more particularly to a device and method for placing an acutely angled bifurcated stent graft through a single access incision. Expandable surgical devices such as stents or stent grafts are used in a variety of places in the human body to repair aneurysms and to support various anatomical lumens, such as blood vessels, respiratory ducts, gastrointestinal ducts, and the like.

Conventionally, these devices are deployed across an aneurysm or in the regions of a stenosis in the target body lumen to repair the aneurysm or to hold the lumen open. Because stent graft implantation is a relatively non-invasive procedure, it has been proven to be a favorable alternative to surgery in, for example, the repair of an aneurysm. Bifurcated devices with their trunk and branching configuration are particularly well suited for use in branching body lumen systems, such as in the coronary vasculature, and the peripheral vasculature. The coronary vasculature includes the right, left common, left anterior descending and circumflex arteries and their branches. The peripheral vasculature includes branches of the carotids, aorta, femoral, popliteal, internal iliac, or hypergastric and related arteries. Placement of such a bifurcated device can be rather complicated, and often involves approaching the bifurcated section of the artery through at least two side branches or through the trunk plus one side branch. The procedure is not only time consuming, but can also lead to more incision sites in the patient's body and can necessitate more complicated maneuvers for the surgeon. These complications are further exaggerated when an acutely angled or reverse direction side branch is accessed, as for example a repair of the hypergastric artery. U.S. Pat. No. 6,645,242 teaches a bifurcated intravascular stent graft comprising primary stent segments and a primary graft sleeve forming a main fluid channel and having a side opening therethrough.

However, there exists a need for a stent graft delivery system which would allow placement of bifurcated stent grafts into acutely angled vasculature such that simpler surgical procedures are enabled. A simplified surgical procedure would decrease the number or size of incisions, reduce the required surgical steps, and thereby reduce patient trauma associated with a more complex medical procedure.

SUMMARY OF THE INVENTION

The present invention further provides an interventional delivery system comprising: a first catheter having at its distal end a side branch vessel segment; a second catheter attached around the first catheter and having at its distal end a main vessel segment; and a side branch vessel device attached to the side branch vessel segment of the first catheter wherein the main vessel segment and the side branch vessel device are simultaneously delivered to a treatment site, and further wherein the second catheter has an opening in a side wall near the distal end of the second catheter to allow for passage of the side branch vessel segment of the first catheter. The second catheter may comprise a capture tube which surrounds the bifurcated guidewire and facilitates for the ease of bifurcated guidewire removal from a vessel. A bifurcated guidewire with at least two distal tips may be used with the first catheter. The two distal tips face opposing directions, wherein one of the two distal tips is the leading end and one of the tips is a reverse facing tip end.

The present invention further provides a first catheter having at its distal end a side branch vessel segment; a second catheter attached around the first catheter and having at its distal end a main vessel segment; a side branch vessel device attached to the side branch vessel segment of the first catheter; and a main vessel device attached to the main vessel segment of the second catheter. The main vessel device and the side branch vessel device are simultaneously delivered to a treatment site.

A method of deploying a branched stent assembly is also provided comprising: advancing a catheter assembly on a bifurcated guidewire to a treatment site; orienting the catheter assembly in the main vessel; pulling the bifurcated guidewire to orient the guidewire reverse facing tip into the side branch vessel; deploying the main vessel device in the main vessel; then advancing the side branch vessel device to a desired location; and deploying the side branch device. After stent deployment, removal of the delivery assembly is facilitated by advancing the guidewire and first catheter forward until the guidewire reverse facing tip and reverse facing portion of the first catheter are retracted from the side branch vessel allowing removal of the bifurcated guidewire along with the first and second catheters.

DESCRIPTION OF THE DRAWINGS

FIG. 2A depicts a bent shaft configuration and FIG. 2B depicts a shaft configuration using a connector.

FIG. 3 shows the bifurcated guidewire assembly with a leading segment and a reverse facing segment.

FIGS. 6A and 6B show side views of a second catheter with a side branch opening.

FIGS. 10A and 10B show partial cross-sectional views of the distal device portion and the proximal hub portions of the interventional delivery system of the present invention. The distal device portion is positioned within a main vessel adjacent to a branched vessel.

FIGS. 11A and 11B show partial cross-sectional views of the distal device portion and the proximal hub portions of the interventional delivery system of the present invention. The reverse facing guidewire is shown being advanced into the side branch, acutely angled vessel.

FIGS. 12A and 12B show partial cross-sectional views of the distal device portion and the proximal hub portions of the interventional delivery system of the present invention. The main body stent is shown in an expanded state.

FIGS. 13A and 13B show partial cross-sectional views of the distal device portion and the proximal hub portions of the interventional delivery system of the present invention. The reverse facing segment of the first catheter with a constrained side branch device is shown being advanced into the side branch, acutely angled vessel.

FIGS. 16A and 16B show partial cross-sectional views of the distal device portion and the proximal hub portions of the interventional delivery system of the present invention. The first catheter, the second catheter, and the guidewire are shown being withdrawn from the treatment site.

DETAILED DESCRIPTION OF THE INVENTION

Figure 1:
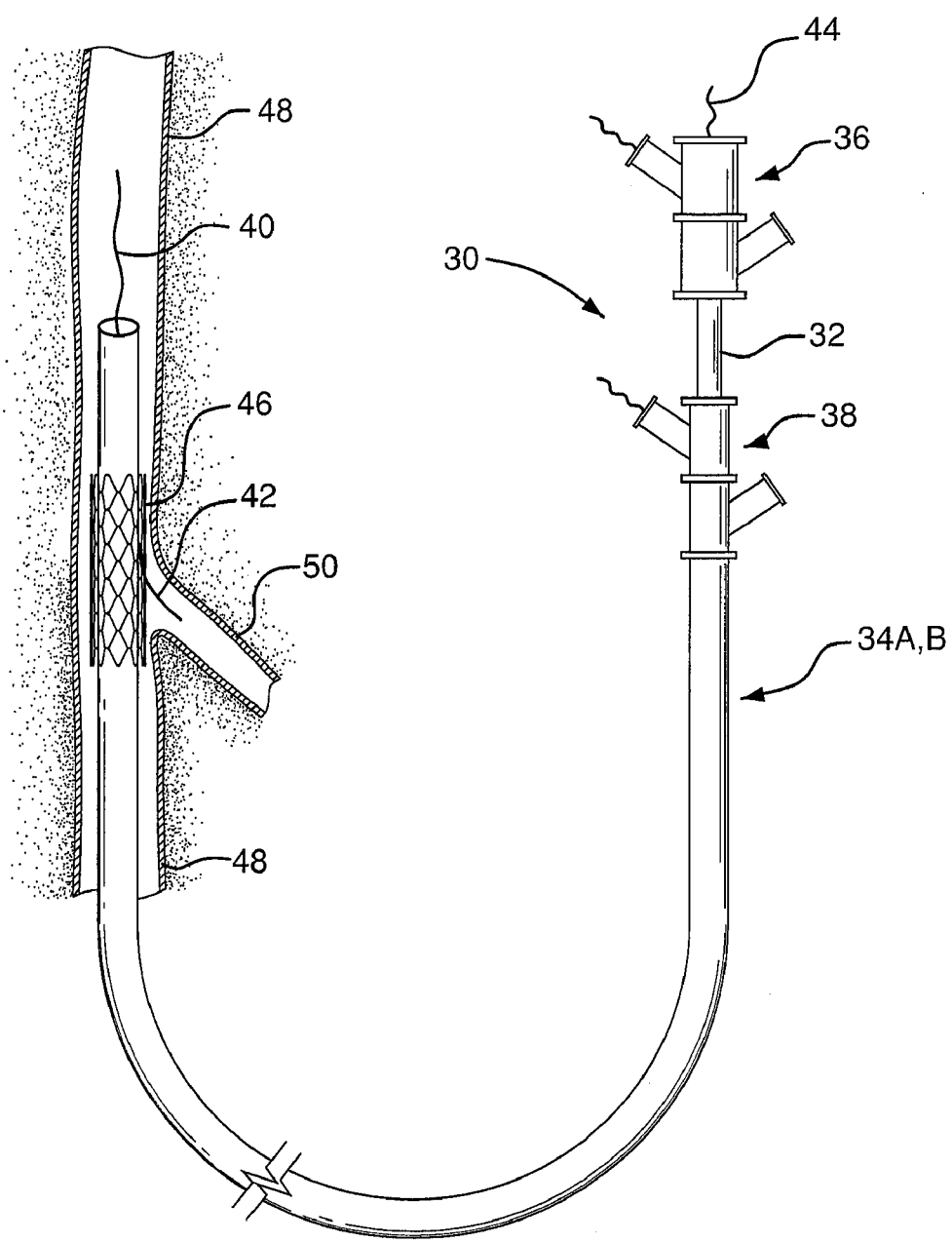
FIG. 1 shows the interventional delivery system comprising a first catheter and a second catheter upon insertion in a vessel.

The present invention provides an interventional delivery system for the placement of bifurcated stent grafts into acutely angled vasculature. Acutely angled vasculature may exist in renal vessels, subclavian arteries, biliary ducts, prostate vessels, and other non-vascular applications as well. The challenge in stent placement is deployment from a main vessel such as a femoral artery to a reverse acute angle vessel. The present invention provides a device and procedure which decreases the number and size of incisions required to place bifurcated stent grafts into acutely angled vasculature, and further reduces the required surgical steps and patient trauma associated with this traditionally more complex medical procedure. As shown in FIG. 1, the present invention provides an interventional delivery system 30 comprising a first catheter shaft 32, a second catheter assembly 34A or 34B, a first catheter hub assembly 36, a second catheter hub assembly 38, a bifurcated guidewire leading tip 40, a bifurcated guidewire reverse facing tip 42, a bifurcated guidewire proximal tip 44, and a device assembly 46. The interventional delivery system 30 is shown positioned in an anatomical main vessel 48 so that the device assembly 46 is positioned approximate to an anatomical side branch vessel 50. As described in subsequent figures, the device assembly 46 will be deployed to form a main body stent within the main vessel 48 along with an integrated side branch stent within the side branch vessel 50.

Shown in FIGS. 2 through 9 are various sub-components and assemblies of the interventional delivery system 30 (of FIG. 1). Shown in FIG. 2A is a first catheter assembly 52A having a first catheter hub assembly 36. The hub assembly 36 includes a perfusion port 54, a bifurcated guidewire port 56, a side branch deployment line 58 protruding from a deployment line port 60. The first catheter assembly 52A further comprises a first catheter shaft 32 that has an apex opening 62A. Apex opening 62A as shown is a cut-opening through the wall of the first catheter shaft 32. The first catheter shaft is shown bent about the apex opening 62A, forming a reverse facing segment 64. The reverse facing segment 64 has a side branch device portion 66 and a side branch device to apex opening separation length 68.

Figure 2A:
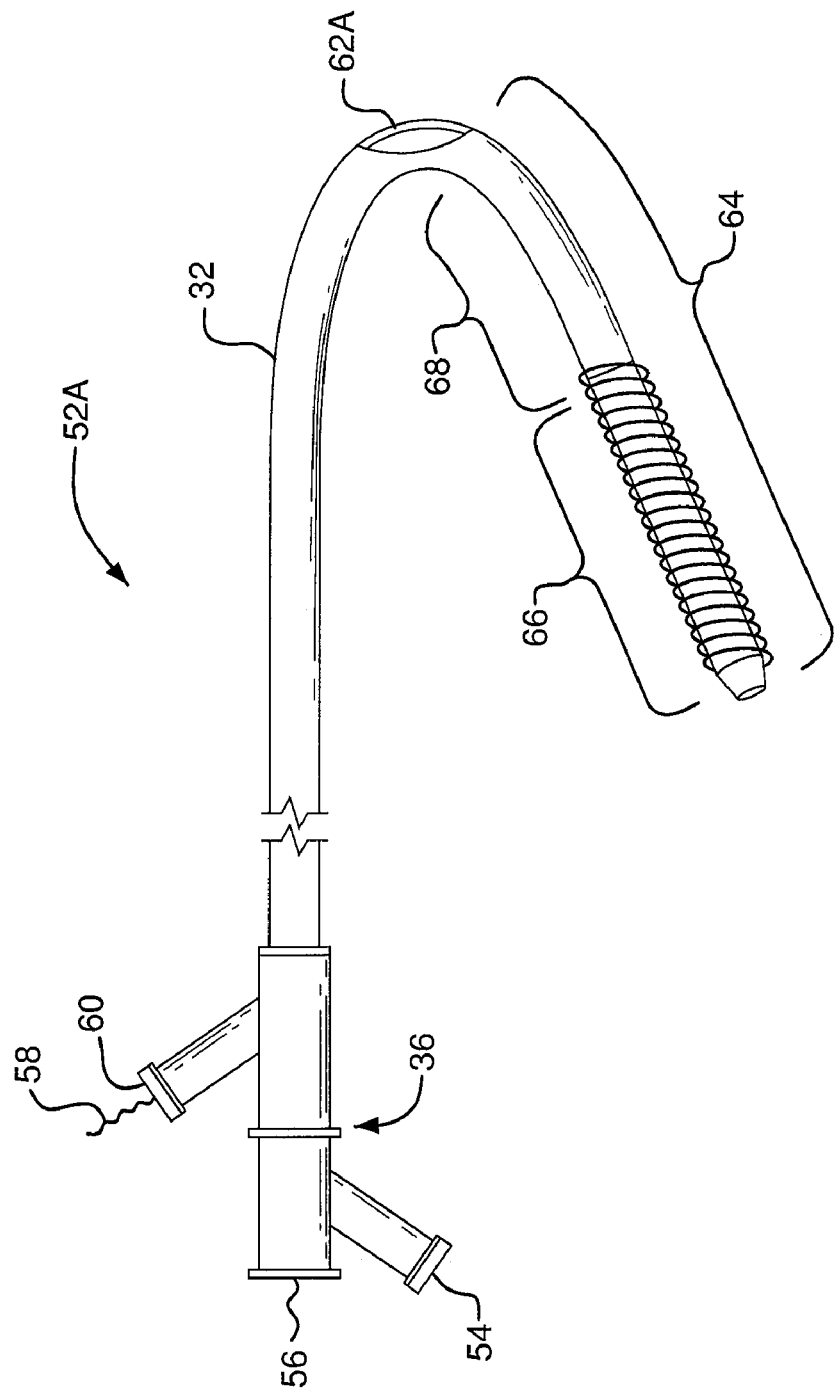
FIGS. 2A and 2B show the first catheter of the interventional delivery system.
Figure 2B:
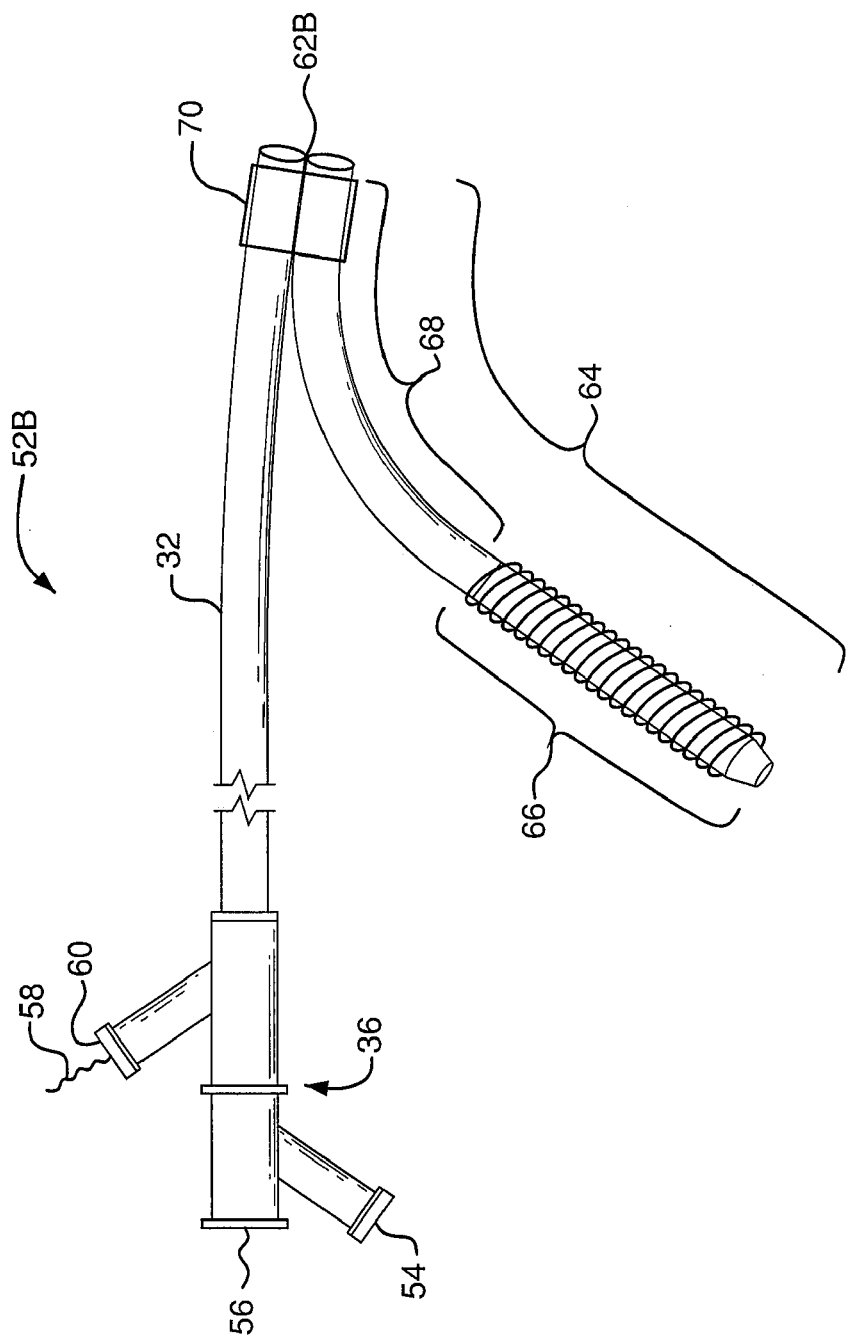

As shown in FIG. 2B a first catheter assembly 52B has a first catheter hub assembly 36. The hub assembly 36 includes a perfusion port 54, a bifurcated guidewire port 56, a side branch deployment line 58 protruding from a deployment line port 60. The first catheter assembly 52B further comprises a first catheter shaft 32 that has an apex opening 62B. Apex opening 62B as shown comprises the open ends of a cut catheter shaft 32. The two cut ends are joined at connection 70. The two cut shafts as shown form a reverse facing segment 64. The reverse facing segment 64 has a side branch device portion 66 and a side branch device to apex opening separation length 68.

Depicted in FIG. 3 is a bifurcated guidewire assembly 72 having a proximal tip and a main segment 76. Within the distal portion of the guidewire main segment 76 is a connection 78, defining a leading guidewire segment 80 and a reverse facing guidewire segment 82. The leading guidewire segment has a leading tip and the reverse facing guidewire segment has a reverse facing tip.

Figure 4A:
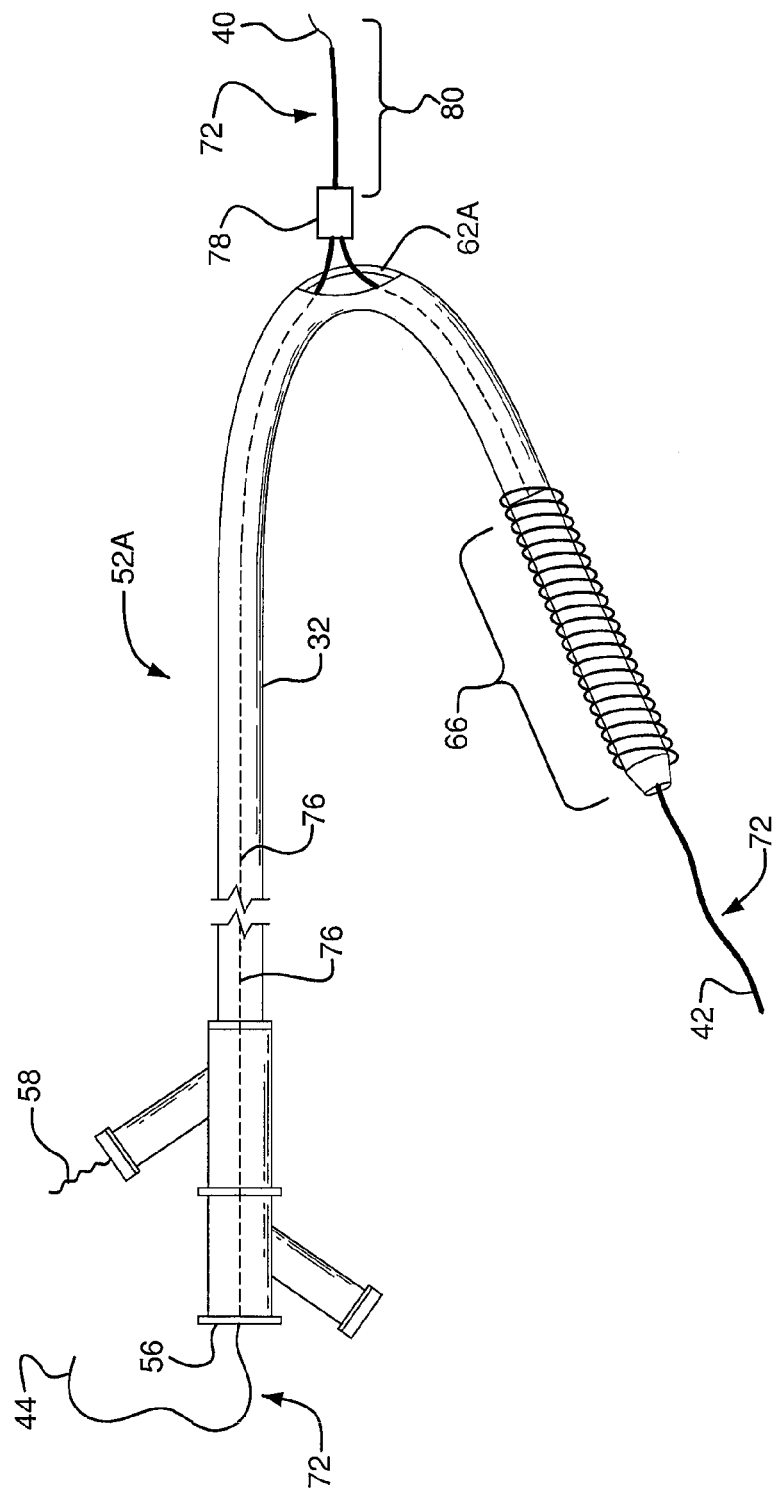
FIG. 4A shows a first catheter with a bent shaft and apex opening for the bifurcated guidewire with a side branch device mounted on the side branch vessel segment of the first catheter shaft.

FIG. 4A shows a first catheter assembly (52A of FIG. 2A) combined with a bifurcated guidewire assembly (72 of FIG. 3). Referring to FIGS. 2A, 3, and 4A, shown is a bifurcated guidewire assembly 72 positioned within a first catheter assembly 52A. Shown protruding from an apex opening 62A is the bifurcated guidewire connection 78 along with the leading guidewire segment 80. The proximal end of the bifurcated guidewire protrudes from the bifurcated guidewire port 56 and the reverse facing tip of the guidewire protrudes from the reverse facing segment of the first catheter.

Figure 4B:
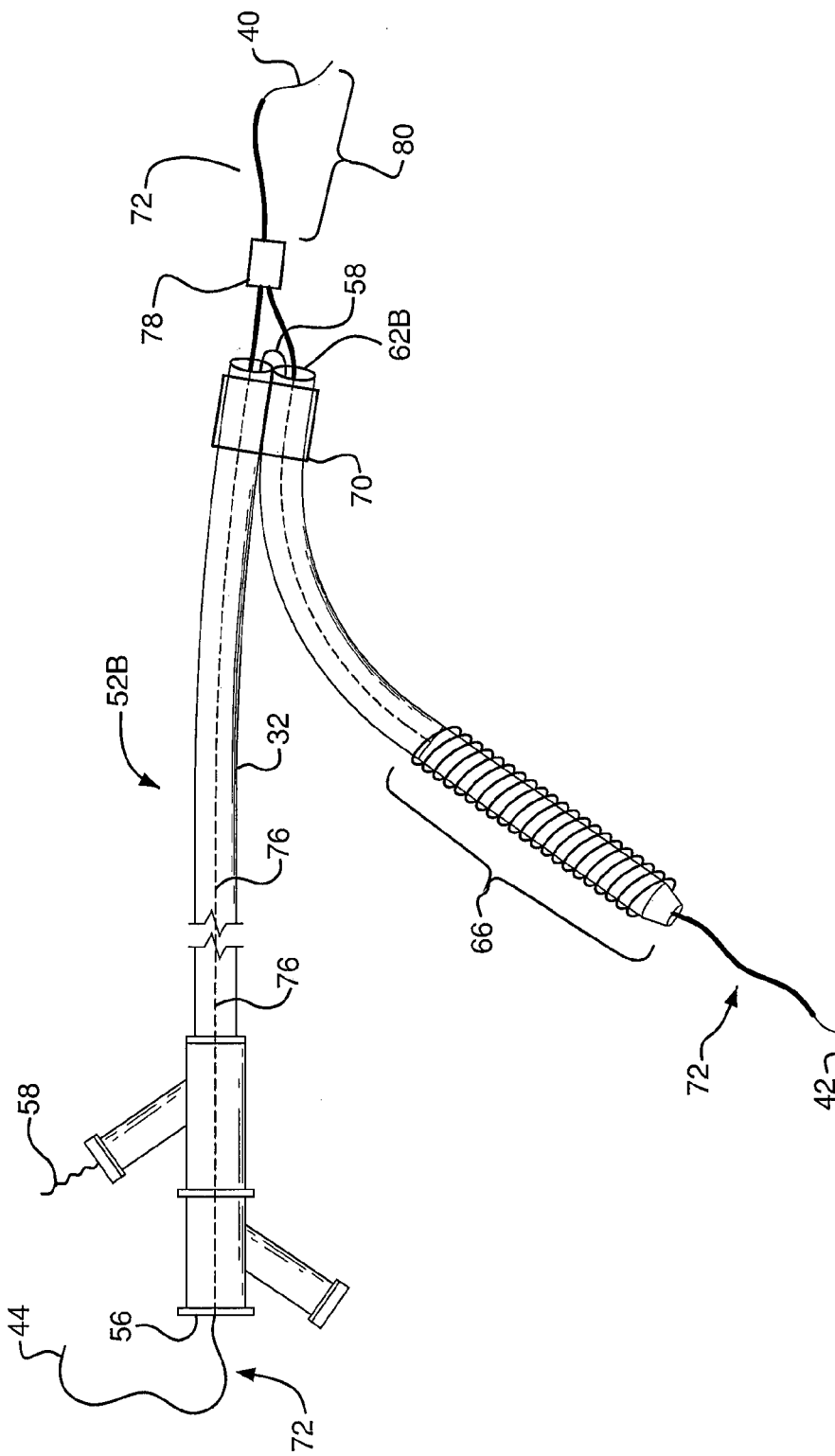
FIG. 4B shows a first catheter with a shaft configuration using a connector for the bifurcated guidewire with a side branch device mounted on the side branch vessel segment of the first catheter shaft.

Similarly, FIG. 4B shows a preferred first catheter assembly (52B of FIG. 2B) combined with a bifurcated guidewire assembly (72 of FIG. 3). Referring to FIGS. 2B, 3, and 4B, shown is a bifurcated guidewire assembly 72 positioned within a first catheter assembly 52B. Shown protruding from an apex opening 62B is the bifurcated guidewire connection 78 along with the leading guidewire segment 80. The proximal end of the bifurcated guidewire protrudes from the bifurcated guidewire port 56, and the reverse facing tip of the guidewire protrudes from the reverse facing segment of the first catheter. The tube-to-tube connection 70 can include a friction-reducing component or feature to allow the deployment line 58 to easily slide against the tubes or apex opening as the deployment line is activated.

Figure 5:
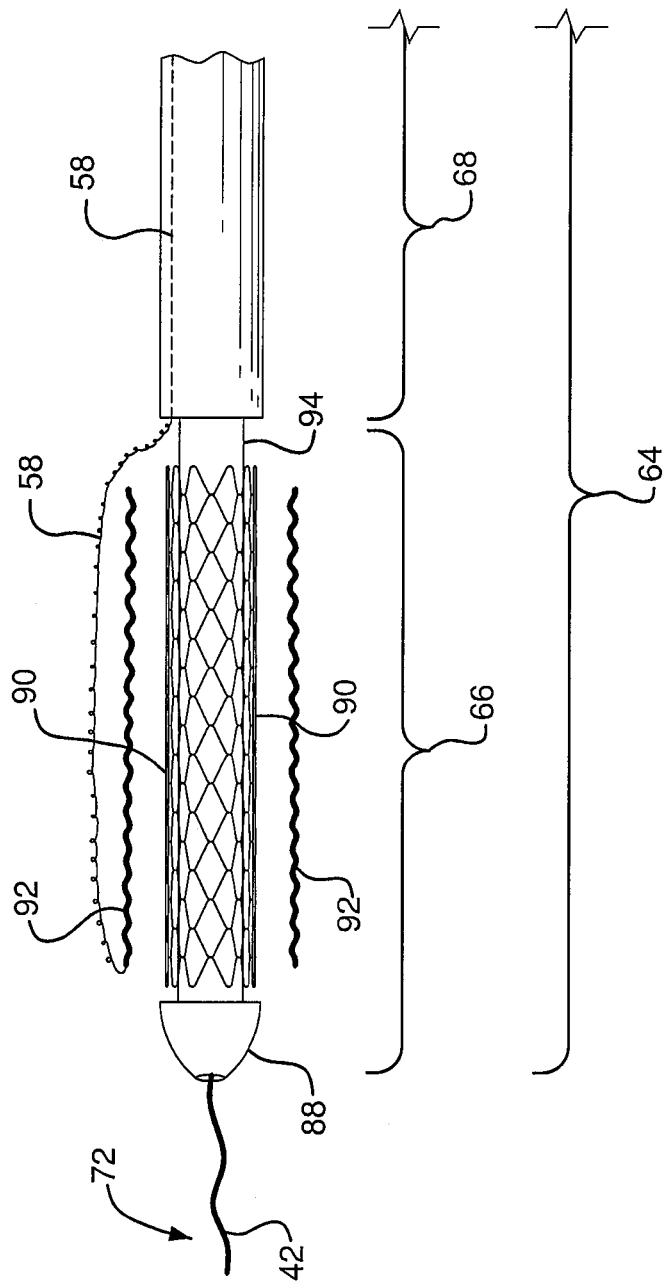
FIG. 5 shows an enlarged view of the side branch vessel segment with a side branch vessel device mounted and constrained within a sheath.

Shown in FIG. 5 are a partial cross-sectional view of the reverse facing segment 64 that includes a side branch device portion 66 and a side branch device to apex opening separation length 68. Shown is the bifurcated guidewire 72 reverse facing tip 42 exiting from an olive 88. Positioned onto a side branch accommodating segment 94 is a constrained, self-expanding side branch device 90. The side branch device 90 is held in a compressed state by a constraining sheath 92. Attached or integral to the constraining sheath is a side branch device deployment line 58.

FIGS. 6A and 6B are side views of two embodiments of a second catheter. Shown in FIG. 6A is a second catheter assembly 34A having a second catheter hub assembly 38. The second catheter hub assembly further includes a proximal perfusion port 54. The hub assembly is joined to a second catheter main body 96. Near the distal end of the second catheter main body 96 is a side branch device opening 98, formed by a cut-out portion of the catheter wall. The opening 98 allows a bifurcated guidewire and a side branch device to be subsequently advanced from the second catheter. After deployment, the bifurcated guidewire can be pulled through the opening 98 into the second catheter for removal. At the distal end of the second catheter main body is a capture tube portion 100. This tube portion "captures" the bifurcated guidewire after device deployment, allowing for a non-traumatic removal of the guidewire and delivery system.

Similarly, FIG. 6B depicts an alternate embodiment of a second catheter assembly 34B. The distal end of the second catheter main body 96 is joined to the capture tube portion 100 by at least one main body to capture tube joining member 102. The main body 96 and the capture tube 102 are therefore separated and connected by the joining members 102. The gap between the main body and the capture tube forms an opening 98 functionally similar to the opening 98 shown in FIG. 6A.

Figure 7:
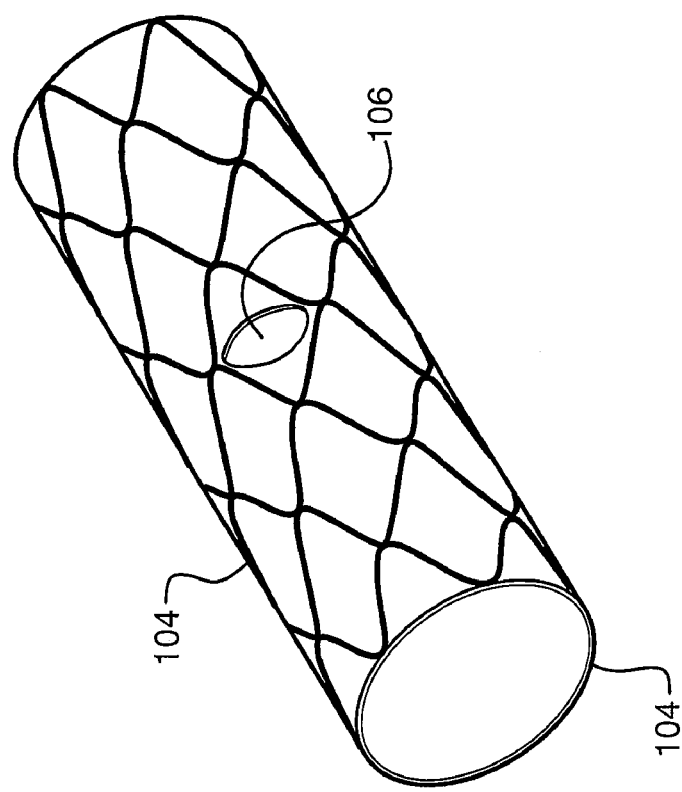
FIG. 7 is an isometric view of an expanded main body stent graft.

FIG. 7 is an isometric view of an expanded main body device 104. An aperture 106 is formed in the main body device wall, permitting a side branch device to be subsequently inserted through and attached to the aperture/main body.

Figure 8:
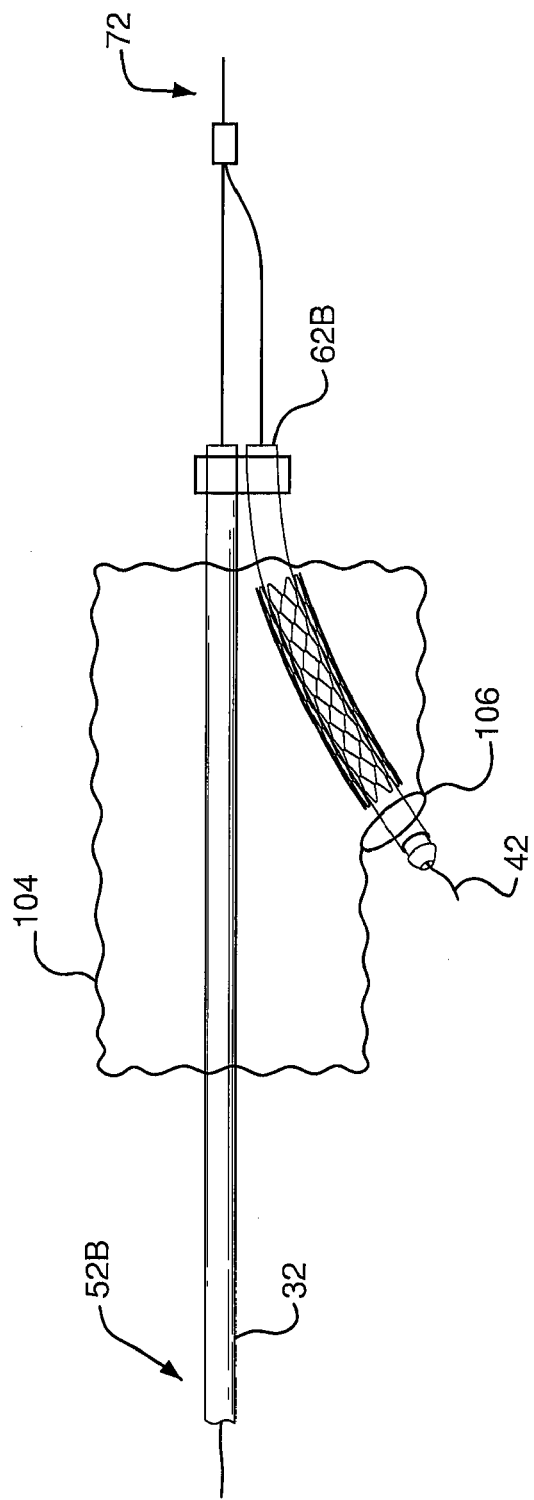
FIG. 8 is a partial cross-sectional view of a main body stent with a bifurcated guidewire and a first catheter with a side branch device.

FIG. 8 is a partial cross-sectional view of a main body device 104 surrounding a first catheter assembly 52B. A bifurcated guidewire 72 is positioned within the first catheter (as previously shown in FIG. 4B). A reverse facing portion of the first catheter having a constrained side branch device is shown protruding through an aperture 106 in the main body stent. Exiting from the reverse facing portion of the first catheter is the reverse facing tip 42 of the bifurcated guidewire. Also shown are the first catheter shaft 32 and the apex opening 62B.

Figure 9:
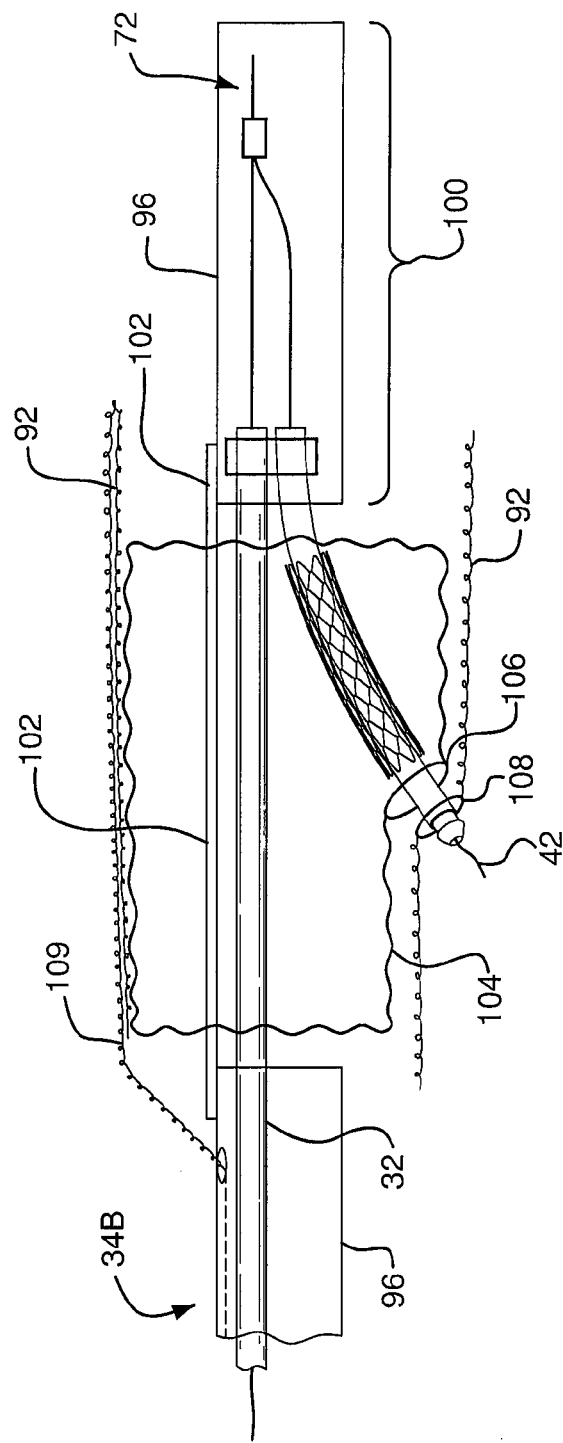
FIG. 9 is a partial cross-sectional view of a main body stent with a bifurcated guidewire and a first catheter with a side branch device contained in a second catheter. Also shown is a constraint sheath over the main body stent and the apertures in the main body stent and the constraining sheath.

FIG. 9 is a partial cross-sectional view of the components depicted in previous FIG. 8 along with a second catheter 34B (refer to FIG. 6B). Shown is a second catheter main body 96, connected to a capture tube portion 100 by at least one joining member 102. The distal end of the bifurcated guidewire is shown positioned within the capture tube portion 100. The first catheter shaft 32 is shown positioned within the second catheter main body 96. Also shown are a constraining sheath 92 and the attached or integral main body deployment line 109. The reverse facing portion of the first catheter is shown protruding through an aperture 108 within the constraining sheath 92.

A sequence used to deliver and deploy main body and side branch stents according to the present invention is depicted in FIGS. 10 through 16.

Deployment Step 1

FIG. 10A is a partial cross-sectional view of the distal end of an interventional delivery system similar to that of FIG. 1. A device assembly is shown initially positioned in an anatomical main vessel 48 so that the device assembly is positioned approximate to an anatomical side branch vessel 50. Shown are a bifurcated guidewire leading tip 40 and a bifurcated guidewire reverse facing tip 42. The device assembly (46 of FIG. 1) has been expanded to display the internal components as shown in FIG. 9. FIG. 10B depicts the proximal end of the interventional delivery system, similar to that shown in FIG. 1. Shown are a first catheter hub assembly 36 and a second catheter hub assembly 38.

Deployment Step 2

FIGS. 11A and 11B show the bifurcated guidewire reverse facing tip 42 being advanced into the side branch vessel 50 along the direction indicated by arrow 110. The guidewire reverse facing tip 42 is advanced by pulling (in direction indicated by arrow 112) on the proximal end of the guidewire.

The two hub assemblies 36, 38 are held stationary as the proximal end of the guidewire is pulled. As the proximal end of the guidewire is pulled, the guidewire leading tip 40 is advanced towards the apex opening 62B in the direction shown by arrow 114. The guidewire reverse facing tip 42 is therefore forced to advance into the side branch vessel 50 in the direction of arrow 110.

Deployment Step 3

Referring to FIGS. 12A and 12B, the main body stent 104 is deployed by pulling on the main body stent deployment line 109 in the direction indicated by arrow 116. By releasing the constraining sheath (92 of FIG. 9) the main body stent is allowed to self-expand in the directions indicated by arrows 118. The two hub assemblies 36, 38 are held stationary as the deployment line is pulled. Note that the guidewire and/or the side branch device are positioned through the aperture 106 in the main body device 104.

Deployment Step 4

The side branch device is then advanced into the side branch vessel, as depicted in FIGS. 13A and 13B. The side branch device is advanced along the direction indicated by arrow 120 by holding stationary the second catheter hub assembly 38 while concurrently pulling on the guidewire proximal tip 44 and the first catheter hub assembly 36. The guidewire may be optionally locked onto the first catheter hub assembly 36 to facilitate this step. As the guidewire and hub assembly are pulled, the distal tip of the guidewire 40 is pulled in the direction indicated by arrow 124, forcing the side branch device to advance partially through the main body device aperture 106 and into the side branch vasculature 50 in the direction 120.

Deployment Step 5

Figure 14A:
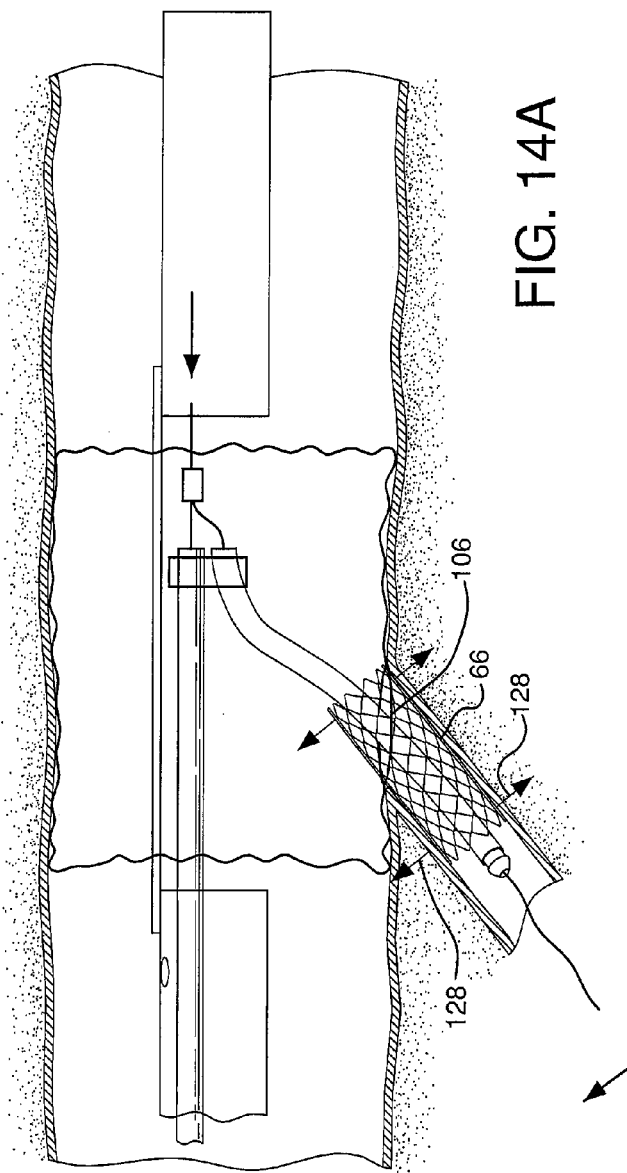
FIGS. 14A and 14B show partial cross-sectional views of the distal device portion and the proximal hub portions of the interventional delivery system of the present invention. The side branch stent is shown in an expanded state.
Figure 14B:
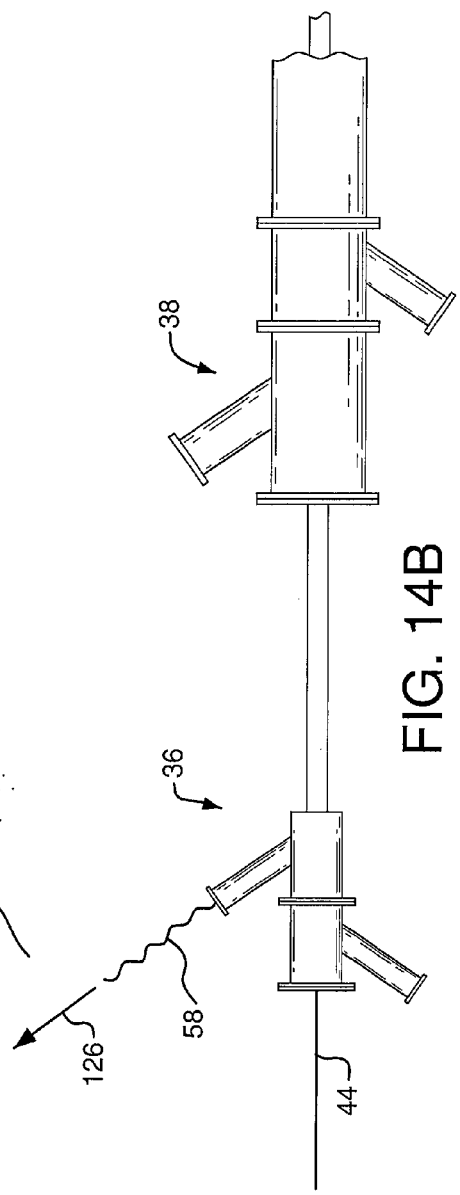

As shown in FIGS. 14A and 14B, the side branch deployment line 58 is then pulled in the direction indicated by arrow 126, allowing the side branch device 66 to self-expand as indicated by arrows 128. Note that the side branch device is partially contained within and constrained by the main body device aperture 106. The two hub assemblies 36, 38 are held stationary as the deployment line is pulled.

Deployment Step 6

Figure 15A:
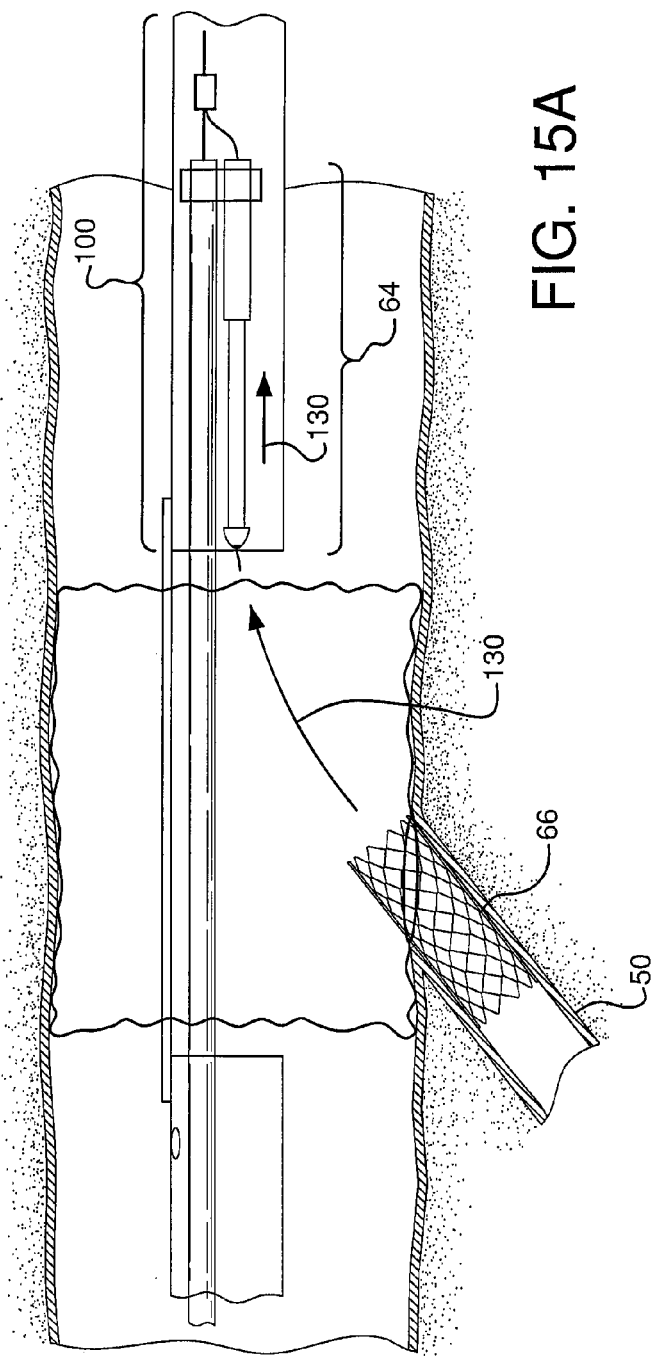
FIGS. 15A and 15B show partial cross-sectional views of the distal device portion and the proximal hub portions of the interventional delivery system of the present invention. The reverse facing portion of the first catheter and the guidewire are shown being advanced into a capture tube.
Figure 15B:
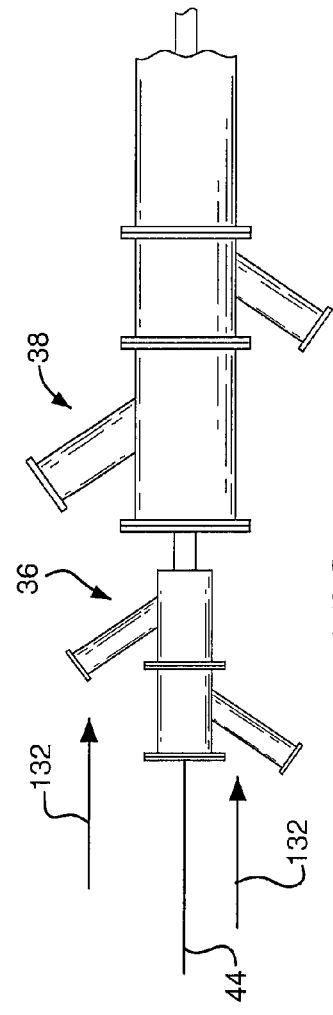

Referring to FIGS. 15A and 15B, the delivery system of the present invention is withdrawn from the vasculature by forcing the reverse facing portion of the first catheter 64 out of the expanded side branch device and into the capture tube 100 along the direction as indicated by arrows 130. The first catheter reverse facing portion is driven into the capture tube by pushing the first catheter hub assembly 36 along with the guidewire proximal tip 44 along the direction as shown by arrows 132. The second catheter hub assembly 38 is held stationary as the first catheter hub assembly and the guidewire are advanced.

Deployment Step 7

To complete the delivery of the devices and systems of the present invention, the first catheter hub assembly 36, the guidewire proximal tip 44, and the second catheter hub assembly 38 are concurrently pulled in the direction as shown by arrows 134 of FIGS. 16A and 16B. The capture tube 100, containing the bifurcated guidewire and the reverse facing portion or the first catheter 64 are non-traumatically removed from the vasculature, leaving the expanded main body device 104 and the attached side branch device 66 in the vasculature.

Referring back to FIG. 7, the main body device 104 is shown with a single side-wall aperture 106. In an alternate configuration, a main body device can have two, three, four, five, six or more side branch apertures. The various catheters of the present invention can incorporate more than one device; for example, a first catheter can incorporate two or more side branch devices. The sealing or interference fit between a main body and a side branch device can be enhanced by the incorporation of a "sealing sleeve". See for example U.S. Pat. No. 6,645,242 to Quinn for a disclosure of such sealing sleeves. Multiple sealing sleeves can be incorporated into a main body device to enhance the sealing or attachment of multiple side branch devices. Sealing sleeves can be "internal to" or "external to" the lumen of a main body stent and can be shaped and sized to seal a specifically configured side branch device.

Stents used in the present invention can be bare (uncovered), coated with a variety of drug eluting, anti-thrombogenic or other coatings, or can include a partial or full cover (as in a stent graft). Anchoring mechanisms, such as barbs, "fish-scales", biological attachment means, or other features can be incorporated into the main body and/or a side branch device to facilitate anchoring to the vasculature.

Main body stents and/or side branch stents can have a uniform profile or have non-uniform profiles such as tapers, "trumpet-end" shapes, "dog-bone" shapes, curves or other profiles that enhance the device performance within a particular treatment site. Multiple devices of the present invention can be "ganged" or interconnected to form a multi-component system. Devices of the present invention can include features that allow or enhance the interconnection or "docking" between multiple devices.

Radiopaque markers or indicators can be incorporated into a main body device, the various catheters used in the present invention and/or a side branch device to facilitate placement and visualization within the vasculature.

Devices of the present invention can be used to treat nonvascular conduits, hollow or tubular parts of organs, such as bilary, bladder, urethra, gastrological, bronchi, bile, and other ducts. Devices of the present invention are particularly suited for, but not limited to, side branch vessels that have an "acute" angle from the main body (see for example FIG. 1).

Devices of the present invention can be balloon-expandable as well as self-expanding. For example, the first catheter according to the present invention can incorporate a balloon (or balloons) and inflation lumens as required to expand a particular device. Combinations of self-expanding and balloon-expandable devices can be configured according to the present invention. Also, separate balloon expanders can be used within the scope of the present invention.

Catheter components of the present invention can be fabricated from common materials such as nylons, polycarbonates, polyethylenes, polypropylenes, polytetrafluoroethylenes, polyvinyl chlorides, polyurethanes, polysiloxanes, stainless steels, nitinols, or other biocompatible materials.

While particular embodiments of the present invention have been illustrated and described herein, the present invention should not be limited to such illustrations and descriptions. It should be apparent that changes and modifications may be incorporated and embodied as part of the present invention within the scope of the following claims.

The invention claimed is:

1. An interventional delivery system for simultaneously delivering a plurality of vessel devices to an acutely angled branched treatment site, said interventional delivery system comprising:
   a first catheter having a catheter shaft with a proximal end and a distal end, a side branch vessel segment extending from the distal end generally toward the proximal end of the catheter shaft, and an apex opening formed between the catheter shaft and the side branch vessel segment;
   a second catheter having a main body with a proximal end and a distal end, the main body being disposed around at least a portion of the first catheter
   a side branch vessel device attached to the side branch vessel segment of the first catheter;
   a main vessel device attached to the distal end of the second catheter main body;
   and a bifurcated guidewire having a main segment extending through the catheter shaft and terminating at a connection point, the bifurcated guidewire having a leading tip and a reverse facing tip each extending from the connection point, the leading and reverse facing tips extending in generally opposite directions, wherein the leading tip extends through the apex opening and the reverse facing tip extends into the side branch vessel segment, the reverse facing tip being axially slidable within the side branch vessel segment in response to selective axial displacement of the main segment of the bifurcated guidewire relative to the catheter shaft.

2. The interventional delivery system of claim 1 wherein a portion of the distal end of the first catheter is folded back on itself to form the side branch vessel segment.

3. The interventional delivery system of claim 1 wherein the first catheter is movable relative to the second catheter between a first position, in which the side branch vessel device is substantially disposed within the main vessel device, and a second position, in which at least a portion of the side branch device extends outwardly through a side opening in the main vessel device, the reverse facing tip guiding the movement of the side branch vessel device between the first and second positions.

4. The interventional delivery system of claim 3, wherein the second catheter has an opening in a side wall near the distal end of the second catheter, which, in the second position, receives the side branch vessel segment of the first catheter and the side branch device therethrough.

5. An interventional delivery system comprising:
   a first catheter having at its distal end a side branch vessel segment, and an apex opening between the distal end and the side branch vessel segment;
   a bifurcated guidewire with at least two distal tips facing in generally opposite directions, wherein one of the two distal tips is a reverse facing tip which is configured to move slidably within the side branch vessel segment of the first catheter, and the other of the two distal tips extends through the apex opening;
   a second catheter disposed around at least a portion of the first catheter and having at its distal end a main vessel segment; and
   a side branch vessel device releasably attached to side branch vessel segment of the first catheter,
   wherein the main vessel segment and the side branch vessel device are simultaneously delivered to a treatment site, and further wherein the second catheter has an opening in a side wall near the distal end of the second catheter, which receives the side branch vessel segment of the first catheter and side branch vessel device therethrough in response to axial displacement of the first catheter relative to the second catheter.

6. The interventional delivery system of claim 5 wherein the side branch vessel segment is passed through the opening and orients at an acute angle to the main vessel segment.

7. The interventional delivery system of claim 6 wherein at least 1 cm of the side branch vessel device is in contact with the main vessel device.

8. An interventional delivery system comprising:

a bifurcated guidewire having a main segment extending toward and terminating at a connection point, the bifurcated guidewire having a leading tip and a reverse facing tip each extending outwardly from the connection point and facing in generally opposite directions;

a first catheter having a lumen slidably receiving the bifurcated guidewire therethrough, the first catheter having an apex opening at its distal end and a side branch vessel segment located adjacent thereto and disposed between the leading and reverse facing tips;

a second catheter extending around the first catheter and having at its distal end an opening, the second catheter having a capture tube adjacent the opening; and a side branch vessel device releasably attached to the side branch vessel segment of the first catheter, wherein the leading tip extends through the apex opening toward the capture tube and the reverse facing tip extends toward the opening in the second catheter, the bifurcated guidewire being selectively movable between a first position, in which the reverse facing tip extends outwardly from the opening in the second catheter for deployment of the side branch vessel device at a treatment site, and a second position, in which both the leading tip and the reverse facing tip are substantially enclosed in the capture tube to facilitate removal from the body after deployment of the side branch vessel device at the treatment site.

* * * * *